United States Patent [19]
DeLuca et al.

[11] Patent Number: 6,071,897
[45] Date of Patent: Jun. 6, 2000

[54] USE OF VITAMIN D COMPOUNDS TO PREVENT TRANSPLANT REJECTION

[75] Inventors: Hector F. DeLuca, Deerfield; Margherita T. Cantorna, Middleton; Colleen E. Hayes, Madison; Debra A. Hullett, Madison; Hans W. Sollinger, Madison; Jean Humpal-Winter, Madison, all of Wis.

[73] Assignee: Wisconsin Alumni Research Foundation, Madison, Wis.

[21] Appl. No.: 09/115,958

[22] Filed: Jul. 15, 1998

Related U.S. Application Data

[63] Continuation-in-part of application No. 08/870,569, Jun. 6, 1997, abandoned, and a continuation-in-part of application No. 08/870,337, Jun. 6, 1997, abandoned.

[51] Int. Cl.[7] .................................................. A61K 31/59
[52] U.S. Cl. ............................................................. 514/167
[58] Field of Search .............................................. 514/167

[56] References Cited

U.S. PATENT DOCUMENTS

| | | | |
|---|---|---|---|
| 4,749,710 | 6/1988 | Truitt et al. . | |
| 5,374,629 | 12/1994 | Calverley et al. | 514/167 |
| 5,387,582 | 2/1995 | Hansen | 514/167 |
| 5,597,815 | 1/1997 | DeLuca et al. | 514/167 |

FOREIGN PATENT DOCUMENTS

| | | |
|---|---|---|
| WO 90/00540 | 1/1990 | WIPO . |
| WO 91/03246 | 3/1991 | WIPO . |

OTHER PUBLICATIONS

T. Cundy, et al., "The Use of Metabolites and Analogues of Vitamin D in Prospective Renal Transplant Recipients," *Clin. Nephrol.* 15(5) :240–245, 1981.

S.C. Jordan, et al., "1,25–Dihydroxyvitamin–D3 Prolongs Rat Cardiac Allograft Survival," *Vitamin D Molecular, Cellular and Clinical Endocrinology*, p. 335, 1988 (Abstract).

S.C. Jordan, et al., "1,25–Dihydroxyvitamin–D3 Prolongs Skin Graft Survival in Mice," *Vitamin D Molecular, Cellular and Clinical Endocrinology*, p. 347, 1988 (Abstract).

E. Lewin and K. Olgaard, "The In Vivo Effect of a New, In Vitro, Extremely Potent Vitamin $D_3$ Analog KH1060 on the Suppression of Renal Allograft Rejection in the Rat," *Calcif. Tissue Int.* 54:150–154, 1994.

P. Veyron, et al., "Two Novel Vitamin D Analogues, KH 1060 and CB 966, Prolong Skin Allograft Survival in Mice," *Trans. Immun.* 1:72–76, 1993.

G. Babany, et al., "Evaluation of the in Vivo Dose–Response Relationship of Immunosuppressive Drugs Using a Mouse Heart Transplant Model: Application to Cyclosporine," *J. Pharmac. Exp. Ther.* 244(1) :259–262, 1988.

R. Bouillon, et al., "Structure–Function Relationships in the Vitamin D Endocrine System," *Endocrine Rev.* 16(2) : 200–257, 1996.

B. Bourbigot, et al., "Bone Histology in Renal Transplant Patients Receiving Cyclosporin," *The Lancet* pp. 1048–1049, 1988.

V.A. Briner, et al., "Prevention of Cancellous Bone Loss but Persistence of Renal Bone Disease Despite Normal 1,25 Vitamin D Levels Two Years after Kidney Transplantation," *Transplantation* 59(10) :1393–1400, 1995.

C. Johnsson, et al., "Immunosuppression With the Vitamin D Analogue MC 1288 in Experimental Transplantation," *Trans. Proc.* 28 (2) :888–891, 1996.

B.A. Julian, et al., "Rapid Loss of Vertebral Mineral Density after Renal Transplantation," *New Eng. J. Med.* 325 (8) : 544–550, 1991.

B.M. Kubak and C.D. Holt, "Infectious Complications of Kidney Transplantation and Their Management," *Handbook of Kidney Transplantation,* 2d Ed., G.M. Danovitch, Little, Brown and Company (Inc.), pp. 187–213, 1996.

J.M. Lemire, et al., "Prolongation of the Survival of Murine Cardiac Allografts by the Vitamin $D_3$ Analogue 1,25–Dihydroxy–$\Delta^{16}$–Cholecalciferol," *Transplantation* 54 (4) :62–63, 1992.

J.M. Lemire, et al., "1,25–Dihydroxy–24–OXO–16ene–Vitamin D3, a Renal metabolite of the Vitamin D Analog 1,25–Dihydroxy–16ene–vitamin D3, exerts Immunosuppressive Activity Equal to its Parent without causing Hypercalcemia in vivo," *Endocrinology* 135 (6) :2818–2821, 1994.

*Primary Examiner*—Kevin E. Weddington
*Attorney, Agent, or Firm*—Quarles & Brady LLP

[57] ABSTRACT

A method of moderating transplant rejection in a transplant recipient comprising administering a dose of vitamin D compound effective to prevent transplant rejection is disclosed. Preferably, the recipient's susceptibility to opportunistic infections has not been compromised. Also preferably, the recipient has not suffered bone demineralization.

34 Claims, 4 Drawing Sheets

USE OF VITAMIN D COMPOUNDS TO PREVENT TRANSPLANT REJECTION

CROSS-REFERENCE TO RELATED APPLICATION

This invention is a continuation-in-part of Ser. No. 08/870,569 filed Jun. 6, 1997 and Ser. No. 08/870,337 filed Jun. 6, 1997, both now abandoned.

STATEMENT REGARDING FEDERALLY SPONSORED RESEARCH OR DEVELOPMENT

This invention was made with United States government support awarded by the following agencies: NIH, Grant No.: DK14881-26S1. The United States has certain rights in this invention.

BACKGROUND OF THE INVENTION 1,25$(OH)_2D_3$ and Analogs

The 1α-hydroxylated metabolites of vitamin D—most importantly 1α,25-dihydroxyvitamin $D_3$ and 1α,25-dihydroxyvitamin $D_2$—are known as highly potent regulators of calcium homeostasis in animals and humans. More recently, their activity in cellular differentiation has also been established. As a consequence, many structural analogs of these metabolites, such as compounds with different side-chain structures, different hydroxylation patterns, or different stereochemistry, have been prepared and tested. Important examples of such analogs are 1α-hydroxyvitamin $D_3$, 1α-hydroxyvitamin $D_2$, various side-chain fluorinated derivatives of 1α,25-dihydroxyvitamin $D_3$, and side-chain homologated analogs. Several of these known compounds exhibit highly potent activity in vivo or in vitro, and possess advantageous activity profiles and thus are in use, or have been proposed for use, in the treatment of a variety of diseases such as renal osteodystrophy, vitamin D-resistant rickets, osteoporosis, psoriasis, multiple sclerosis, and certain malignancies.

1,25-$(OH)_2D_3$ as an Immunomodulator

The first indication that vitamin D might modulate immunity was the discovery that peripheral blood monocytes and activated T lymphocytes have 1,25-dihydroxyvitamin $D_3$ receptors (reviewed in Manolagas, S. C., et al., *Mol. and Cell. Endocrin.* 43:113–122, 1985). Despite many investigations, 1,25-dihydroxyvitamin $D_3$ immunomodulatory activity remains largely undefined and often controversial (reviewed in Manolagas, S. C., et al., supra, 1985; Rigby, W. F. C., *Today* 9:54–57, 1988; and Lemire, J. M., et al., *J. Nutr.* 125:1704S–1708S, 1995).

The action of 1,25-dihydroxyvitamin $D_3$ on human peripheral blood mononuclear cells (PBMC) has been studied extensively in vitro. These in vitro experiments showed that the hormone inhibited mitogen-stimulated proliferation of the PBMC (Lemire, J. M., et al., *J. Clin. Invest.* 74:657–661, 1984; Rigby, W. F. C., et al., *J. Clin. Invest.* 74:1451–1455, 1984) by reducing IL-2 production (Lemire, J. M., et al., *J. Immunol.* 134:3032, 1985; Iho, S., et al., *Immunol. Let.* 11:331–336, 1985; Manolagas, S. C., et al., *J. Clin. Endocrinol. Met.* 63:394, 1986) at the level of gene transcription (Alroy, I., et al., *Mol. Cell. Biol.* 15:5789–5799, 1995). In contrast, Bhalla, et al. (Bhalla, A. K., et al., *J. Immunol.* 133:1748–54, 1984) reported that the hormone did not inhibit mitogen-stimulated mouse spleen and thymus cell proliferation, although it did inhibit antigen-stimulated proliferation of these cells. Lacey, et al. (Lacey, D. L., et al., *J. Immunol.* 138:1680–1686, 1987) reported that the hormone actually stimulated mitogen-induced proliferation of cloned mouse T-cells. No studies have directly addressed the action of the hormone on T lymphocyte differentiation and function in vivo.

Disparate results have been reported for T lymphocyte IFN-γ synthesis in vitro. Rigby, et al. (Rigby, W. F. C., et al., *J. Clin. Invest.* 79:1659–1664, 1987) and Reichel, et al. (Reichel, H., et al., *Proc. Natl. Acad. Sci. USA* 84:3387–3389, 1987) showed that 1,25-dihydroxyvitamin $D_3$ decreased IFN-γ synthesis in mitogen-stimulated PBMC. However, Muller, et al. (Muller, K., et al., *Immunol. Let.* 35:177–182, 1993) reported that the hormone had no effect on IFN-γ synthesis in human T-cell lines. The hormone inhibited cytotoxic T lymphocyte development but not cytotoxic function (Merino, F., et al., *Cell. Immunol.* 118:328–336, 1989).

There is controversy about 1,25-dihydroxyvitamin $D_3$ action on monocyte/macrophage cells in vitro. 1,25-dihydroxyvitamin $D_3$ enhanced a myeloid leukemia cell's differentiation to the macrophage phenotype (Manolagas, S. C., et al., supra, 1985). It also increased monocyte/macrophage production of M-CSF, TNF-α, and prostaglandin E2, but decreased IL-12 synthesis (Lemire, J. M., et al., *FASEB J.* 8:A745 (abs), 1994). The hormone decreased macrophage costimulatory function for T-cell proliferation (Rigby, W. F. C. and M. G. Waugh, *Arthritis Rheum.* 35:110–119, 1992). Disparate results have been reported for 1,25-dihydroxyvitamin $D_3$ effects on IL-1 synthesis in vitro. The hormone decreased IL-1 synthesis in some reports (Iho, S., et al., supra, 1985; Tsoukas, C. S., et al., *J. Clin. Endocrinol. Metab.* 69:127–133, 1989) and increased IL-1 synthesis in other reports (Amento, E. P., *J. Clin. Invest.* 73:731–739, 1987; Bhalla, A. K., et al., *Immunol.* 72:61–64, 1991; Fagan, D. L., et al., *Mol. Endocrinol.* 5:179–186, 1991). Likewise, some investigators reported that 1,25-dihydroxyvitamin $D_3$ enhanced class II protein expression in vitro (Morel, P. A., et al., *J. Immunol.* 136:2181–2186, 1986) but others reported that it decreased class II protein expression (Amento, E. P., supra, 1987; Carrington, M. N., et al., *J. Immunol.* 140:4013–4018, 1988; Rigby, W. F. C., et al., *Blood* 76:189–197, 1990). Together these findings provide no clear and consistent view of how 1,25-dihydroxyvitamin $D_3$ might modify macrophage function. No studies have directly addressed the action of the hormone on monocyte/macrophage differentiation and function in vivo.

There is also controversy about 1,25-dihydroxyvitamin $D_3$ action on B lymphocytes (reviewed in Rigby, W. F. C., supra, 1988). Lemire, et al. (Lemire, J. M., et al., supra, 1984) reported that the hormone inhibited mitogen-stimulated IgG and IgM synthesis by human peripheral blood mononuclear cells. Suppressive and enhancing effects of 1,25-dihydroxyvitamin $D_3$ on mitogen-stimulated B cell proliferation and on antibody synthesis in vitro have been shown. In vivo, 1,25-dihydroxyvitamin $D_3$ has been reported to enhance antibody synthesis in some studies (Abe, J., et al., *Endocrinology* 124:2645–2647, 1989; Ross, T. K., et al., *Vitamins Hormones* 49:281–326, 1994; Daynes, R. A., et al., *Infec. Immun.* 64:1100–1109, 1996) and to inhibit it in other studies (Lemire, J. M., et al., supra, 1995).

Lemire, et al., *Transplantation* 54:762–763, 1992 have described prolongation from 7 to 16 days of the survival of murine cardiac allografts by the vitamin $D_3$ analog 1,25-dihydroxy-delta 16-cholecalciferol. The effective dose of this analog caused severe hypercalcemia. Other analogs showed some prolongation, but also caused hypercalcemia.

Johnsson, et al., *Transplant. Proc.* 28:888–891, 1996 30 described prolongation of survival from 3 to 14 days by administration of the vitamin D analog MC 1288 in Wistar/

Kyoto rat cardiac allografts. These workers concluded that the analog worked best in combination with cyclosporin. The analog increased survival from 8–11 days but also induced hypercalcemia.

1,25-dihydroxyvitamin $D_3$ (1,25($OH)_2D_3$) treatment have been tested by others for their ability to prolong experimental transplanted cardiac graft survival. Lemire, et al., supra, 1992 used the murine cardiac graft model and showed that 1,25($OH)_2D_3$ did not prolong graft survival. In a review, Bouillon (Bouillon, et al., *Endocrine Review* 16 [2] 200–257, 1995) cites one experiment in the rat where cardiac grafts were prolonged briefly with 1,25($OH)_2D_3$ treatments (6 control days versus 10 treated days). The dose of 1,25($OH)_2D_3$ necessary for this minimal graft prolongation was 500 ng/kg/day given intraperitoneally. The overall conclusion from these experiments was that unmodified 1,25($OH)_2D_3$ alone does not prolong graft survival.

BRIEF SUMMARY OF THE INVENTION

The present invention is a method of moderating transplant rejection in a transplant recipient by administering an amount of a vitamin D compound, preferably 1,25($OH)_2D_3$ or analogs thereof, effective to induce the acceptance of foreign grafts. The method comprises selecting a patient and administering a sufficient amount of the vitamin D analog to the patient such that the rejection of the transplanted organ is moderated.

In a particularly advantageous form of the invention, susceptibility to opportunistic infection is not increased and bone demineralization is prevented.

In a particularly advantageous form of the method, the administered compound is either 1α,25-dihydroxyvitamin $D_3$ (1,25-($OH)_2D_3$), 19-nor-1,25-dihydroxyvitamin $D_2$ (19-nor-1,25-($OH)_2D_3$), 24-homo-22-dehydro-22E-1α,25-dihydroxyvitamin $D_3$ (24-homo-22-dehydro-22E-1,25-($OH)_2D_3$), 1,25-dihydroxy-24(E)-dehydro-24-homo-vitamin $D_3$ (1,25-($OH)_2$-24-homo $D_3$), or 19-nor-1,25-dihydroxy-21-epi-vitamin $D_3$ (19-nor-1,25-($OH)_2$-21-epi-$D_3$) In a most preferred form of the invention, the compound is 1,25($OH)_2D_3$.

A preferred dose of vitamin D compound for the present invention is the maximum that a patient can tolerate and not develop serious hypercalcemia.

If the vitamin D compound is not a 1α-hydroxy compound, a particularly advantageous daily dose of vitamin D compound is between 10.0 and 100 μg per day per 160 pound patient. If the vitamin D compound is a 1α-hydroxy compound, the preferred dose is between 0.25 and 50 μg per day per 160 pound patient. If the patient has calcium intakes above 800 mg/day, doses of 1,25($OH)_2D_3$ over 0.75 μg per day per 160 pound patient are not preferred. If the patient is on a low calcium diet and/or takes the dose late at night, higher doses of 1,25($OH)_2D_3$ would be possible and would be preferred. In this embodiment of the invention, the amount of 1,25($OH)_2D_3$ administered could be as high as 1.5 μg per day per 160 pound patient. A preferred dose would be 0.5-1.0 μg per day per 160 pound patient.

It is an advantage of the present invention that the method moderates transplant rejection.

It is another advantage of the present invention that the method increases transplant survival.

It is another advantage of the present invention that the method moderates transplant graft survival without increasing the risk of opportunistic infection.

Is another advantage of the present invention that the method increases transplant survival without increasing the risk of opportunistic infection and without bone demineralization of the patient.

It is another advantage of the present invention that the method moderates transplant rejection without bone demineralization of the patient.

Other advantages and features of the present invention will become apparent after examination of the specification, claims and drawings.

DETAILED DESCRIPTION OF THE INVENTION

The present invention is a method of treating human transplant patients by administering an amount of a vitamin D compound, preferably 1,25($OH)_2D_3$ or analogs thereof, effective to diminish rejection symptoms. The method comprises selecting a transplant patient and administering a sufficient amount of the vitamin D analog to the patient such that the rejection symptoms are abated or moderated. By "moderated" we mean that transplant survival is significantly increased by the administered compound.

Our results indicate that 1,25($OH)_2D_3$ treatments can increase transplant survival relative to an untreated recipient. However, immunosuppressive agents are usually not given as a single modality. In contrast, most transplant centers use triple or quadruple maintenance therapy. Thus, 1,25($OH)_2D3$ (or analog) would typically be given as a part of maintenance therapy in which one of the components would be decreased or deleted (probably prednisone). To monitor efficacy, 1,25($OH)_2D_3$ treatment would be compared to standard therapy for the number of acute biopsy-proven rejection episodes during the first 6 months and for diminished or no increased toxicity. Preferably, the patient would be monitored for reduced acute rejection with decreased or no opportunistic infections and decreased bone loss.

By "significantly increased" survival, we mean that the comparisons would indicate that organ survival rate would be at least 10%, preferably 20%, and most preferably 30% higher.

We have discovered that 1,25($OH)_2D_3$ does not act as simple immunosuppressant but as a selective modulator of immune responses allowing appropriate resistance to infection while providing a means for tolerance of any transplants differing in histocompatibility.

Further, unlike other drugs used to allow transplant survival, we have discovered the analogs of 1,25($OH)_2D_3$ do not cause bone demineralization but instead improve bones of the transplant recipient.

In a particularly advantageous form of the invention, the administered compound is either 1α,25-dihydroxyvitamin $D_3$ (1,25-$(OH)_2D_3$), 19-nor-1,25-dihydroxyvitamin $D_2$ (19-nor-1,25-$(OH)_2D_3$), 24-homo-22-dehydro-22E-1α,25-dihydroxyvitamin $D_3$ (24-homo-22-dehydro-22E-1,25-$(OH)_2D_3$), 1,25-dihydroxy-24(E)-dehydro-24-homo-vitamin $D_3$ (1,25-$(OH)_2$-24-homo $D_3$), or 19-nor-1,25-dihydroxy-21-epi-vitamin $D_3$ (19-nor-1,25-$(OH)_2$-21-epi-$D_3$).

In another form of the present invention, the vitamin D compound has the formula wherein $X^1$ and $X^2$ are each selected from the group consisting of hydrogen and acyl; wherein $Y^1$ and $Y^2$ can be H, or one can be O=aryl or O=alkyl and can have a β or α configuration; $Z^1=Z^2=H$ or $Z^1$ and $Z^2$ together are $CH_2$; and wherein R is an alkyl, hydroxyalkyl or fluoroalkyl group, or R may represent the following side chain:

wherein (a) may have an S or R configuration, $R^1$ represents hydrogen, hydroxy or O-acyl, $R^2$ and $R^3$ are each selected from the group consisting of alkyl, hydroxyalkyl and fluoralkyl, or, when taken together represent the group $(CH_2)_m$ wherein m is an integer having a value of from 2–5, $R^4$ is selected from the group consisting of hydrogen, hydroxy, fluorine, O-acyl, alkyl, hydroxyalkyl and fluoralkyl, wherein if $R^5$ is hydroxyl or fluoro, $R^4$ must be hydrogen or alkyl, $R^5$ is selected from the group consisting of hydrogen, hydroxy, fluorine, alkyl, hydroxyalkyl and fluoroalkyl, or $R^4$ and $R^5$ taken together represent double-bonded oxygen, $R^6$ and $R^7$ taken together form a carbon-carbon double bond, $R^8$ may be H or $CH_3$, and wherein n is an integer having a value of from 1 to 5, and wherein the carbon at any one of positions 20, 22, or 23 in the side chain may be replaced by an O, S, or N atom.

In an especially preferred form of the compound, $R^2$ and $R^3$ are selected from the group consisting of alkyl, hydroxyalkyl and fluoralkyl.

One may evaluate a candidate vitamin D compound for its suitability for the present invention. Preferably, the candidate compound should first be subjected to an initial mouse-model screening procedure, such as that described below for 1,25-$(OH)_2D_3$ in the Examples below. A successful compound will reduce transplant rejection symptoms in mice, preferably to the extent shown in the Examples for 1,25-$(OH)_2D_3$. However, a successful compound is generally described as one that increases survival of the transplant by at least 10%, preferably 20%.

Preferably, the compound should also show a significant reduction in either opportunistic infection and bone demineralization compared to cyclosporin A treated transplant recipients. The Examples below describe experimental models for the measurement of opportunistic infection and bone demineralization. These compounds would then be predicted to be successful in human patients.

The Examples below demonstrate that animals treated with vitamin D compounds are no more susceptible to opportunistic infections than control animals.

The Examples below also demonstrate that animals treated with vitamin D analogs do not show decreased total and percent bone ash. In fact, preferably, the vitamin D analog treatments increase total and percent bone ash.

A preferred dose of vitamin D compound for the present invention is the maximum that a patient can tolerate and not develop serious hypercalcemia.

If the vitamin D compound is not a 1α-hydroxy compound, a particularly advantageous daily dose of vitamin D compound is between 10.0 and 100 μg per day per 160 pound patient.

If the vitamin D compound is a 1α-hydroxy compound, the preferred dose is between 0.5 and 50 μg per day per 160 pound patient. If the patient has normal calcium intakes, doses of a 1α-hydroxy compound, such as 1,25-$(OH)_2D_3$, over 0.75 μg per day per 160 pound patient are not preferred. If the patient is on a low calcium diet and/or takes the dose late at night, higher doses of 1,25-$(OH)_2D_3$ would be possible and would be preferred. In this embodiment of the invention, the amount of 1,25-$(OH)_2D_3$ administered could be as high as 1.5 μg per day per 160 pound patient. A preferred dose would be 0.5–1.5 μg per day per 160 pound patient.

1,25-dihydroxyvitamin $D_3$ (1,25-$(OH)_2D_3$) is currently administered at a level of 0.5 μg/day per 160 pound patient, usually in two quarter microgram capsules morning and night for the treatment of osteoporosis or renal osteodystrophy. In countries where dietary calcium is of the order of 800 mg/day or even up to 1,000 mg/day, higher doses of 1,25-$(OH)_2D_3$ cannot be used because the dose results in increased urinary calcium and increased plasma calcium with the danger of hypercalcemia and resultant deterioration of the kidney, calcification of the heart, lung, aorta, and other soft tissues.

Therefore, the maximum preferred dose of 1,25-$(OH)_2D_3$ would appear to be at 0.5 μg/day. However, higher doses can be used under circumstances when dietary calcium is of the order of 600 mg/day. Other less active 1α-hydroxy vitamin D compounds can be given at higher doses safely. For example, in Japan the treatment of osteoporosis with 1,25-$(OH)_2D_3$ is 0.5 to 0.75 μg/day. The same is true of other low calcium countries, such as Italy, where as much as 1 mg/day of 1,25-$(OH)_2D_3$ has been successfully used by Dr. Caniggia (Caniggia, A., et al., *Metabolism* 39:43–49, 1990).

We believe that to increase transplant success, a higher dose of 1,25-$(OH)_2D_3$ would be most helpful. Calcium intake can be reduced to approximately 400–500 mg/day by merely eliminating dairy products and calcium supplements from the diet. Furthermore, the dose of 1,25-$(OH)_2D_3$ can be given at night before bedtime, i.e. 10 p.m., and because of the time of appearance of this compound in the circulation, calcium absorption would be at a minimum, allowing for larger doses of 1,25-$(OH)_2D_3$.

A preferred treatment regime would be the following: Before the transplant procedure, reduce the patient's calcium intake to about 500 mg/day by eliminating all supplements of calcium and also reducing the consumption of dairy products, providing for a dietary intake of calcium of 500 mg. Vitamin D treatment should start at least 5 days before the transplant procedure. If, under these circumstances, the 1,25-(OH)$_2$D$_3$ is also administered at 10 p.m., the dose of 1,25-(OH)$_2$D$_3$ can be safely increased to up to 1 μg or perhaps 2.0 μg/day.

The preferred mode of treatment for 1α-hydroxy compounds is administration under regular dietary circumstances of 0.5–0.75 μg/day of the compound. A preferred method would be to administer 0.75–1 μg/day at 10 p.m. or before bedtime. A most preferred method would be to both reduce the dietary calcium intake to 400–500 μg/day and to administer between 0.75 and 1.5 μg/day at 10 p.m.

A preferred mode of treatment for non-1α-hydroxy compounds would also be administration under regular dietary circumstances. In this case, the treatment dose could be increased up to 100 μg/day per 160 pound patient.

By "transplant rejection" we mean disease symptoms characterized by loss of organ function. Thus, a kidney rejection would be indicated by a rising creatinine level in blood and by means of a biopsy. Heart rejection is indicated by an endomyocardial biopsy, while pancreas rejection is determined by biopsy and rising blood glucose. Liver rejection is indicated by measurements of transaminases of liver origin, bilirubin levels in blood and by biopsy. Intestine rejection is determined by biopsy, while lung rejection is determined by measurement of blood oxygenation.

The present invention is appropriate for all organ transplants, preferably heart, liver, kidney, pancreas, lung and intestines. Skin grafts, because of their unique immunological issues, are not organ transplants as defined by the present invention.

EXAMPLES

A. Reduction of Opportunistic Infection After Transplant

1. In General

We compared 1,25-(OH)$_2$D$_3$ and cyclosporin A treatment in their ability to prevent cardiac transplant rejection. Because cyclosporin A is the major anti-rejection drug in use, it is chosen as the comparative standard for evaluation of new transplant drugs (Jubak, B. M., and C. D. Colt, "Handbook of Kidney Transplantation," *Infection Complications of Kidney Transplantation and their Management*, Danovitch, G. M. editor, pp. 187–213).

In addition, we determined whether the identical doses of 1,25-(OH)$_2$D$_3$ and cyclosporin A diminished the ability of the host to resist infection with *Candida albicans* and *Herpes simplex* viruses(HSV). The *C. albicans* and HSV were used as pathogens to measure host resistance because transplant patients on broadly immunosuppressive drugs (such as cyclosporin A) often develop fungal and viral infections. *C. albicans* infections are one of the more common infections in immunosuppressed individuals (Jubak, B. M., and C. D. Colt, supra). Similarly, members of the Herpesviridae family of viruses account for a large part of the morbidity and mortality of the immunosuppressed individuals (Jubak, B. M., and C. D. Colt, supra). Members of this family of viruses include HSV, cytomegalovirus (CMV) and Ebstein bar (EB) virus. All human herpes viruses are frequently reactivated following immunosuppressive therapy for organ transplantation (White, D. O., and F. J. Fenner, *Medical Virology Third Edition*, Chapter 16:401).

2. Material and Methods

Animals. B10.A(4R) mouse breeding pairs were obtained from Jackson Laboratories (Bar Harbor, Me.) and bred in the Biochemistry Animal Facility. Unsexed 12–24 hour newborn B10.A(4R) mice were used as cardiac graft donors. Male C57BL/10 (allograft) mice (Sprague Dawley, Indianapolis, Ind.) and male B10.A(4R) (isograft) mice were used as recipients. The donor strain is incompatible with the recipient at one class I locus and two class II loci (B10.A (4R)-H-2 $K^kA_\beta^kA_\alpha^k$, C57BL10-H-2$K^bA_\beta^bA_\alpha^b$).

Treatments. Experimental diets (Yang, S., et al., *Arch. Biochem. Biophys.* 303:98–106, 1993) which contained no vitamin D were made and replaced every 2–3 days for the duration of the experiment as described (Yang, S., et al., supra, 1993). Groups of 9–10 recipients were fed the experimental diet alone, the experimental diet plus an intraperitoneal injection of cyclosporin A (25 mg/kg/day) or the experimental diet that provided 50 ng per mouse per day of 1,25-(OH)$_2$D$_3$. The diets were started one week prior to transplantation or infection. The dose of cyclosporin A was based on the reports of others (Babany, G., et al., *J. Pharmac. Exp. Therap.* 244:259, 1987). A dose of 2.5 mg/kg/day was too low to prolong graft survival in our experiments. A dose of 25 mg/kg/day proved effective. The experimental diets contained normal amounts of calcium (0.47%).

Transplants. The method of Babany, et al. was used (Babany, G., et al., supra, 1987). Recipient mice were anesthetized with etomidate (28 mg/kg intraperitoneal). The donor heart was carefully excised and split in two without removal of the atrium. The recipients' ears were cleaned with 70% alcohol and a 2 mm slit was made to provide a pouch where the donor heart was inserted followed by careful removal of excess fluid and any air. A 16 gauge plastic angiocatheter was used to insert the half-heart into the ear pouch.

Evaluation of transplant viability. The heart grafts were observed daily using magnified (3X) microsurgical glasses by a technician blinded to the treatments. The mice were not anesthetized for these observations. Particular care was taken when scoring onset and cessation of contractile activity to avoid incorrectly scoring a graft. After four successive days on which no contractions were observed the animals were sacrificed, weighed and bled for serum calcium analysis.

Data analysis. The success rate for each group of mice was expressed as the ratio of the total number of recipients with contracting heart grafts to the total number in the group.

*Candida albicans* infections. Groups of 5–6 C57BL10 male mice were injected intravenously with $5 \times 10^6$ *C. albicans* B311 (type A, Dr. Edward Balish, University of Wisconsin, Madison). Systemic candidiasis occurs in immunosuppressed patients following dissemination of *C. albicans* from the alimentary tract (Krause, W., et al., *Lancet* 1:598, 1981). Death due to systemic candidiasis is a result of overwhelming kidney infection which leads to kidney failure (Cantorna, M. T., and E. Balish, *J. Infect. Dis.* 164:936, 1991).

*Herpes simplex* viral (HSV-1) infections. Female Balb/c mice were anaesthetized by inhalation of 3%–5% halothane; the cornea was scratched 3 times vertically and 3 times horizontally with a 27 gauge needle and a 3.5 μl drop of HSV-1 strain DRG4Al (Dr. Curtis Brandy, University of Wisconsin, Madison) virus suspension containing $1 \times 10^6$ plaque forming units/mouse was placed on the eye (Kintner, R. L., and C. R. Brandt, *Curr. Eye Res.* 14:145, 1994). The drop was left for 30 seconds and the eye was closed; any excess media was removed with a cotton swab. The virus causes a local infection, which if not held in check by the immune system, will spread and cause viral encephalitis and death.

3. Results

Figure 1:
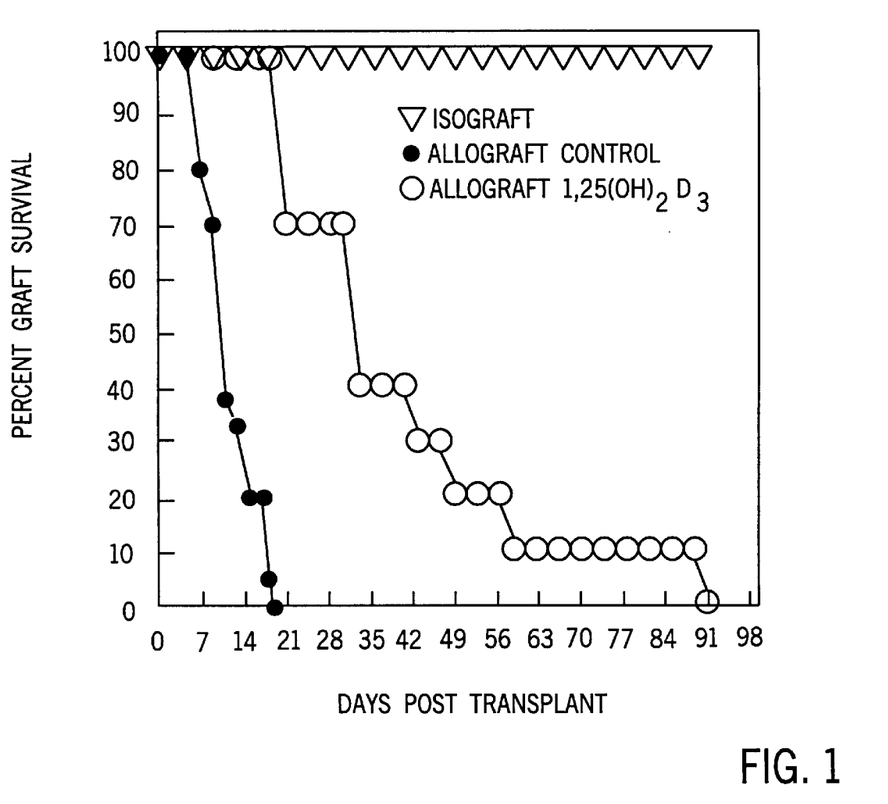
FIG. 1 diagrams the surgery success rate for isografts, allograft control, and allografts in recipients treated with 1,25($OH)_2D_3$.

FIG. 1 describes the success rate for the isografts and the allografts. All of the grafts started contraction within 8 days of surgery. None of the isografts were rejected whereas all of the control allografts were rejected by day 15 post-transplant. Referring to FIG. 1, 1,25-$(OH)_2D_3$ treatment prolonged graft survival significantly. The 1,25-$(OH)_2$D3 treated mice did not reject any grafts until day 18 post-transplant. Forty percent of the 1,25-$(OH)_2D_3$-treated mice had grafts which survived to day 34, and 20% survived to day 50 or more post-transplant. Serum calcium values were in the normal range for both groups (control-8.5±0.6 mg %; 1,25-$(OH)_2D_3$ treated-9.3±0.6 mg %).

Figure 2:
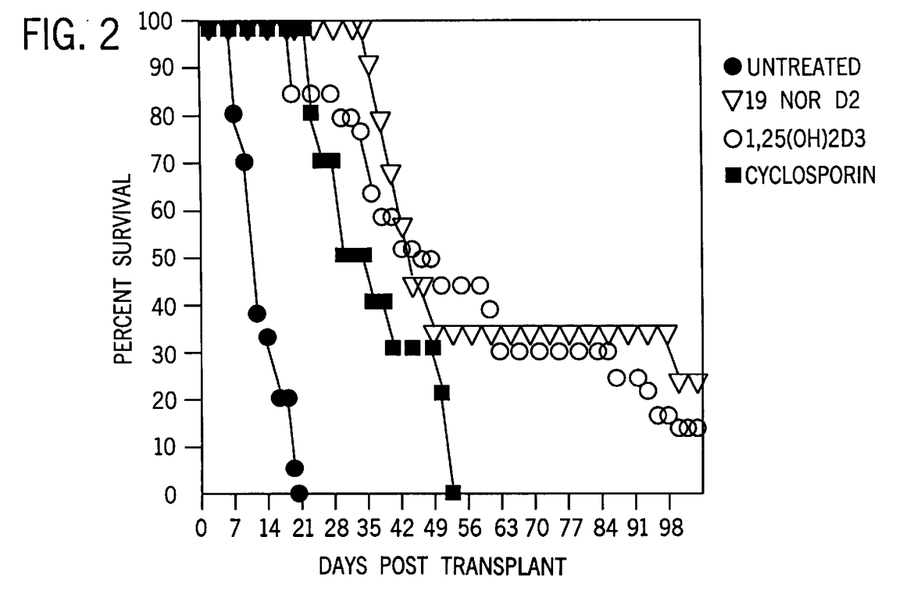
FIG. 2 diagrams transplant success following 1,125(OH)$_2D_3$ and cyclosporin treatment of graft recipients.

FIG. 2 describes transplant prolongation following 1,25-$(OH)_2D_3$ or cyclosporin treatments. Untreated control recipients (●) maintained their grafts for a mean of 9.8 days, saline controls; for 11.6 days (data not shown), 2.5 mg/kg cyclosporin (data not shown) for 11.3 days, and 50 ng 1,25-$(OH)_2D_3$ (○) for 52.2 days. The high dose of cyclosporin 25 mg/kg (■) 34.0 days and 200 ng dose of 19-nor-1,25-$(OH)_2D_2$ (▽) 58.6 days. Importantly 12% of the 1,25-$(OH)_2D_3$-treated and 22% of the 19-nor-1,25-$(OH)_2D_2$-treated mice maintained their grafts over 100 days after transplantation, while all of the cyclosporin-treated mice rejected by day 50. We conclude that 1,25-$(OH)_2D_3$ and analogs are better for preventing transplant rejection and maintaining transplant than cyclosporin.

Figure 4:
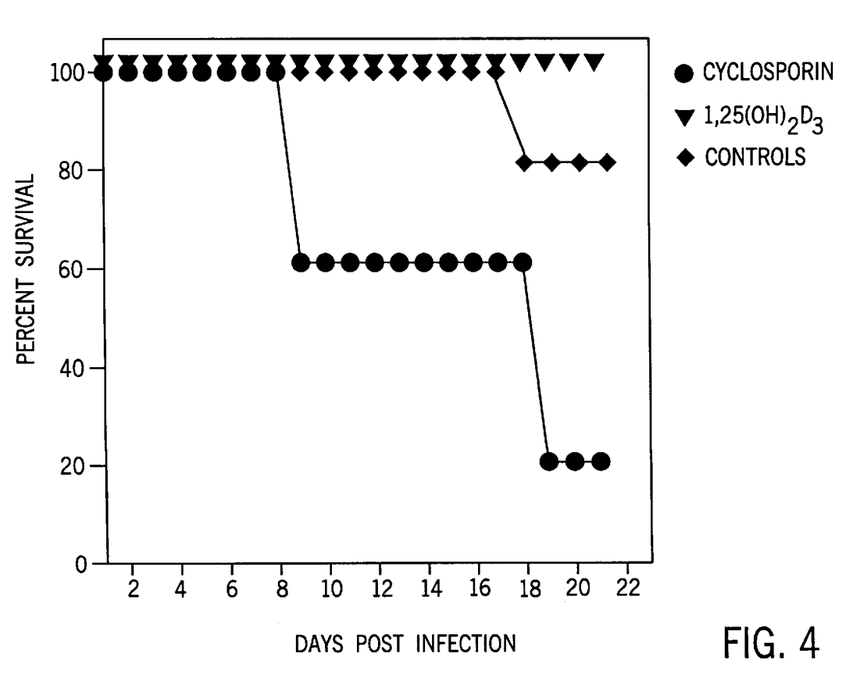
FIG. 4 diagrams mortality following systemic *C. albicans* infection.

FIG. 4 diagrams mortality following systemic C. albicans infections. C57BL10 male mice were infected systematically with C. albicans. These are the identical mice used as transplant recipients in the above experiments. Cyclosporin treatment increased the susceptibility of these mice to C. albicans infection compared to the controls and the 1,25-$(OH)_2D_3$ treated animals. Forty percent of the cyclosporin treated animals died after 9 days of infection while none of the controls or the 1,25-$(OH)_2D_3$ treated mice died. Three weeks of infection left only 20% of the cyclosporin-treated animals alive, 80% of the controls and 100% of the 1,25-$(OH)_2D_3$-treated mice alive. We concluded that 1,25-$(OH)_2D_3$ treatments had no effect on the susceptibility of mice to C. albicans infection.

Figure 5:
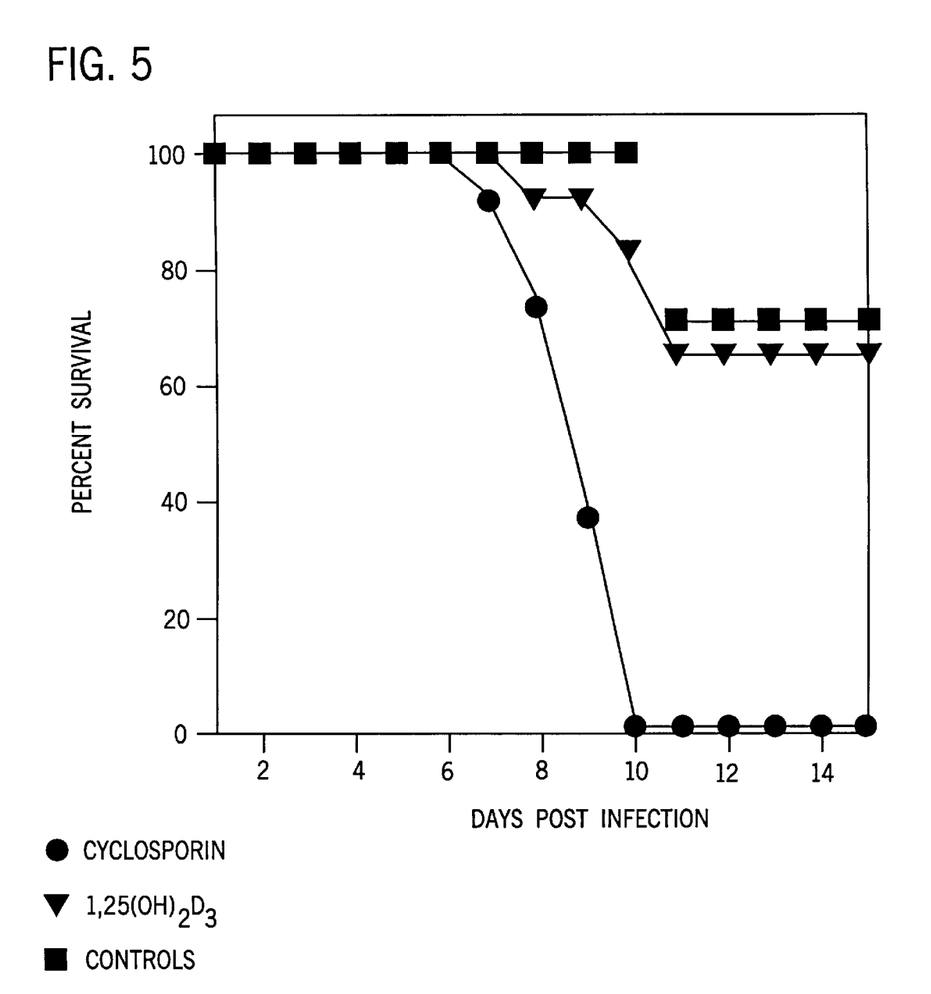
FIG. 5 diagrams mortality following HSV ocular infection.

FIG. 5 diagrams mortality following dissemination of HSV ocular infection. We used Balb/c female mice exactly as described by our collaborators (Kintner, R. L., and C. R. Brandt, supra, 1994). Cyclosporin A treatment increased the susceptibility of these mice to HSV infection compared to the controls and the 1,25-$(OH)_2D_3$ treated animals. One hundred percent of the cyclosporin-treated mice were dead by day 10 post-infection. Conversely, this viral infection disseminated and was lethal for only 30% of the controls and 36% of the 1,25-$(OH)_2D_3$ treated mice. We concluded that 1,25-$(OH)_2D_3$ treatments had no effect on the susceptibility of mice to HSV infection.

B. Transplant Rejection in Adult Rat

To further test the ability of 1,25-$(OH)_2D_3$ to prolong transplant survival, we tested the ability of 1,25$(OH)_2D_3$ to prolong the survival of an adult ACI heart transplanted into an adult Lewis rat. The model represents a directly vascularized model and is considered more stringent. The ACI→LEWIS combination is considered a high responder and the most difficult to transplant. These two strains of rats are genetically unrelated and, therefore, transplants should be rejected rapidly. Transplant survival in this model requires strong "immunosuppressive" drugs.

Animals: Inbred male ACI and Lewis rats were used as donors and recipients. All animals were purchased from Harlan Sprague-Dawley, Inc. (Indianapolis, Ind.). Animals were maintained according to the NIH guidelines and all protocols were approved by the University of Wisconsin Research Animals Resources Committee.

Operative procedure: Donors and recipients were anesthetized with a single injection of chloral hydrate (0.5 ml/100 gm of a 7.5% solution, ip). After heparinization, the donor heart was perfused with cold heparinized UW solution and removed. Donor hearts were transplanted according to the method of Ono and Lindsey as described previously (Fujina, Y., et al., *Transplant* 57:41, 1994).

Treatment: 1,25$(OH)_2D_3$ dissolved in ethanol was added to experimental diet containing no vitamin D as described previously. Recipients were placed on experimental diet with 1,25$(OH)_2$D3 (500 ng/rat/day) one week prior to transplantation and maintained on the diet until the time of rejection. In addition, rats were injected ip with 1,25(OH)$_2D_3$ (500 ng/rat) for the first 4 post-operative days. Recipients were maintained on diet until the time of rejection.

Figure 3:
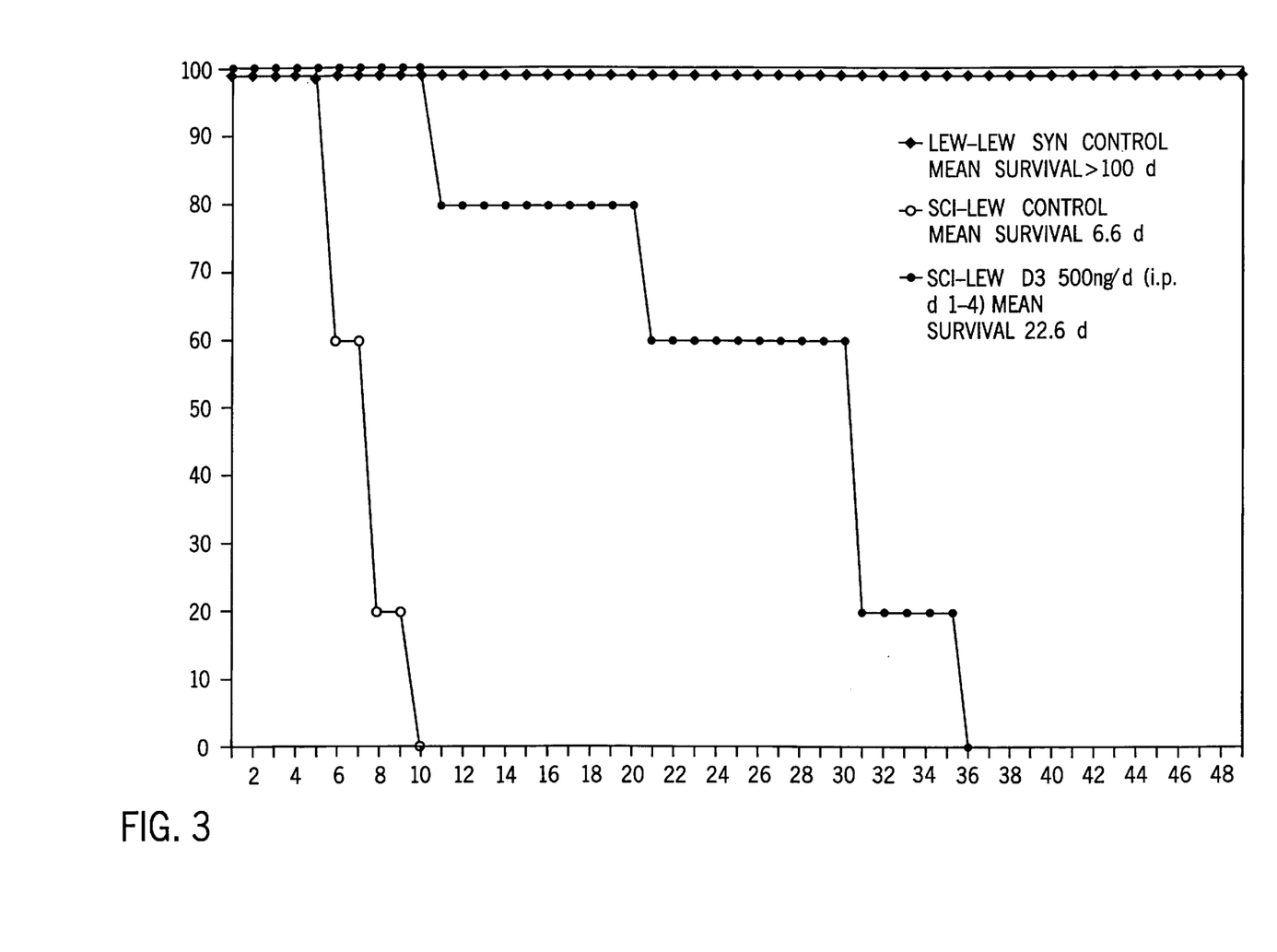
FIG. 3 diagrams the success rate for Lewis to Lewis isographs, ACI to Lewis allografts, and ACI to Lewis allografts in recipients treated with 1,25($OH)_2D_3$.

Results: FIG. 3 shows that the success rate for the transplant surgeries was 100% as shown by the Lewis to Lewis isografts (♦). Control treatment Lewis rats maintained their grafts for a mean of 6.6 days (○). 1,25-$(OH)_2D_3$ treatment prolonged graft survival to a mean of 22.6 days (●). We concluded that 1,25-$(OH)_2D_3$ prolonged adult graft survival in genetically unrelated recipients.

C. Evaluating Bone Loss in Transplant Recipients

1. In General

We collected femurs from all of the transplanted mice to determine whether our treatments resulted in bone loss. A serious side-effect of many immuno-suppressive therapies given to transplant patients is bone loss, brittle bones, and osteopenia (Brener, V. A., et al., *Transplantation* 59:1393, 1995; Julian, B. A., et al., *New Engl. J. Med.* 325:544, 1991).

2. Materials and Methods

Animals. B10.A(4R) mouse breeding pairs were obtained from Jackson Laboratories (Bar Harbor, Me.) and bred in the Biochemistry Animal Facility. Unsexed 12–24 hour newborn B10.A(4R) mice were used as cardiac graft donors. Male C57BL/10 (allograft) mice (Sprague Dawley, Indianapolis, Ind.) and male B10.A(4R) (isograft) mice were used as recipients. The donor strain is incompatible with the recipient at one class I loci and one class II loci (B10.A (4R)-H-2 $K^kA^k$, C57BL10-H-2 $K^bA^b$).

Treatments. Experimental diets (Yang, S, et al., supra, 1993) which contained no vitamin D were made and replaced every 2–3 days for the duration of the experiment. Groups of 9–10 recipients were fed the experimental diet alone, the experimental diet plus an intraperitoneal injection of cyclosporin A (25 mg/kg/day) or the experimental diet that provided 50 ng per mouse per day of 1,25$(OH)_2D_3$. The diets were started one week prior to transplantation or infection. The dose of cyclosporin A chosen was based on the reports of others (Babany, G., et al., supra, 1987). A dose of 2.5 mg/kg/day was too low to prolong graft survival in our experiments. The experimental diets contained normal amounts of calcium (0.6%).

Transplants. The method of Babany, et al. was used (Babany, G., et al., supra, 1987). Recipient mice were anesthetized with etomidate (28 mg/kg intraperitoneal). The donor heart was carefully excised and split in two without removal of the atrium. The recipient's ear was cleaned with alcohol and a 2 mm slit was made to provide a pouch where the donor heart was inserted followed by careful removal of excess fluid and any air. A 16 gauge plastic angiocatheter was used to insert the half heart into the ear pouch.

Evaluation of transplant viability. The heart grafts were observed daily (blindly) using magnified (3X) microsurgical glasses. The mice were not anesthetized for these observations. Particular care was taken when scoring onset and cessation of contractile activity to avoid incorrectly scoring a graft. After four successive days on which no contractions were observed the animals were sacrificed, weighed and bled for serum calcium analysis.

Data analysis. The success rate for each group of mice was expressed as the ratio of the total number of recipients with contracting hearth grafts to the total number in the group.

Bone ash measurements. Femurs were removed from transplanted mice after all of the mice had rejected the donor hearts and had been sacrificed by $CO_2$ suffocation. The mice had been treated with cyclosporin or $1,25(OH)_2D_3$ for 4–8 weeks. The femurs were removed, freed of adhering tissue, tagged for identification and submerged in 100% ethanol for 24 hours. The fluid levels were adjusted periodically to keep the samples completely submerged. The femurs were then removed and submerged in chloroform for an additional 24 hours. The femurs were then placed in pre-weighed crucibles and dried at 100° C. for 12 or more hours. The crucibles and femurs were then cooled in a desiccator, weighed and then ashed at 600° C. for 24 hours in a muffle furnace. After the oven and samples were cooled, they were again placed in a 100° C. over for 12 hours and then desiccated. The ashed femurs were then weighed.

Table 1 records our findings. Low dose (2.5 mg) cyclosporin caused a slight decrease in total bone ash. The high dose (25 mg) of cyclosporin required for the prolongation of graft survival significantly reduced total bone ash value. On the other hand, $1,25(OH)_2D_3$ treatments not only did not decrease bone ash but actually increased both total and percent bone ash. We conclude that cyclosporin treatments that retard transplant rejection (25 mg/kg) induce bone loss, while 1,25(OH)2D3 treatments that increase transplant survival (50 ng/day) actually increase total and percent bone ash.

TABLE 1

Cyclosporin and $1,25(OH)_2D_3$ Bone Ash Comparison

| All mice were fed 0.47% Ca | Dry Bone (mg) ± SEM | Bone Ash (mg) ± SEM | % Ash ± SEM |
|---|---|---|---|
| Group 1 | | | |
| Saline | 36.8 ± 0.7 | 20.2 ± 0.4 | 54.9 ± 0.6 |
| Cyclosporin (2.5 mg/kg) | 34.6 ± 0.8 | 19.4 ± 0.4 | 56.3 ± 0.5 |
| $1,25(OH)_2D_3$ 50 ng/mouse/day | 39.7 ± 0.7 | 23.3 ± 0.4 | 58.7 ± 0.3 |
| Group 2 | | | |
| Saline | 38.9 ± 1.2 | 20.9 ± 0.7 | 53.8 ± 0.4 |
| Cyclosporin (25 mg/kg) | 39.2 ± 0.6 | 17.4 ± 0.2 | 50.4 ± 0.6 |
| $1,25(OH)_2D_3$ 50 ng/mouse/day | 34.6 ± 0.7 | 21.6 ± 0.4 | 55.18 ± 0.6 |

We claim:

1. A method of moderating transplant rejection in a transplant recipient comprising administering an oral dose of vitamin D compound effective to moderate transplant rejection, wherein the recipient's susceptibility to opportunistic infections has not been compromised.

2. The method of claim 1 wherein the infections are selected from the group consisting of C. albicans and HSV.

3. The method of claim 1 wherein the vitamin D compounds are 1α-hydroxy compounds.

4. The method of claim 3 wherein the compound is 1,25 $(OH)_2D_3$.

5. The method of claim 3 wherein the amount of vitamin D analog administered is between 10 and 100 μg per day per 160 pound patient.

6. The method of claim 3 wherein the amount of vitamin D analog administered is between 0.5 and 0.75 μg per day per 160 pound patient.

7. The method of claim 3 wherein the amount of vitamin D analog administered is between 0.5 and 1.5 μg per day per 160 pound person.

8. A method of moderating transplant rejection of a transplant recipient comprising the steps of orally administering to a transplant rejection an amount of the following compound effective to reduce transplant rejection:

wherein $X^1$ and $X^2$ are each selected from the group consisting of hydrogen and acyl;

wherein $Y^1$ and $Y^2$ can be H, or one can be O=aryl or O=alkyl and can have a β or α configuration; $Z^1=Z^2=H$ or $Z^1$ and $Z^2$ together are $CH_2$; and wherein R is an alkyl, hydroxyalkyl or fluoroalkyl group, or R may represent the following side chain:

wherein (a) may have an S or R configuration, $R^1$ represents hydrogen, hydroxy or O-acyl, $R^2$ and $R^3$ are each selected from the group consisting of alkyl, hydroxyalkyl and fluoroalkyl, or, when taken together represent the group $—(CH_2)_m—$ wherein m is an integer having a value of from 2 to 5, $R^4$ is selected from the group consisting of hydrogen, hydroxy, fluorine, O-acyl, alkyl, hydroxyalkyl and fluoroalkyl, wherein if $R^5$ if hydroxyl or fluoro, $R^4$ must be hydrogen or alkyl, $R^5$ is selected from the group consisting of hydrogen, hydroxy, fluorine, alkyl, hydroxyalkyl and fluoroalkyl, or $R^4$ and $R^5$ taken together represent double-bonded oxygen, $R^6$ and $R^7$ taken together form a carbon-carbon double bond, $R^8$ may be H or $CH_3$, and wherein n is an integer having a value of from 1 to 5, and wherein the carbon at any one of positions 20, 22, or 23 in the side chain may be replaced by and O, S, or N atom, wherein the recipient's susceptibility to opportunistic infections has not been comprised.

9. The method of claim 8 wherein the infection is C. albicans and HSV.

10. The method of claim 8 wherein the compound is selected from the group of 1,25-dihydroxyvitamin $D_3$, 19-nor-1,25-dihydroxyvitamin $D_2$, 19-nor-21-epi-1,25-dihydroxyvitamin $D_3$, 1,25-dihydroxy-24-homo-22-dehydro-22E vitamin $D_3$, and 19-nor-1,25-dihydroxy-24-homo-22-dehydro-22E-vitamin $D_3$.

11. The method of claim 8 wherein the amount of compound administered is between 0.5 and 50 μg per day per 160 pound patient.

12. The method of claim 8 wherein the amount of compound administered is between 0.5 and 0.75 μg per day per 160 pound patient.

13. The method of claim 8 wherein the amount of compound administered is between 0.5 and 1.5 μg per day per 160 pound patient.

14. The method of claim 8 wherein the dose is given orally.

15. The method of claim 8 wherein the patient is on a low calcium diet.

16. The method of claim 8 wherein the administering is at night.

17. The method of claim 8, wherein the dose is given orally and wherein the patient is on a low-calcium diet and wherein the dose is 0.5–3.0 μg 1,25-dihydroxyvitamin $D_3$/day or its analog equivalent.

18. A method of moderating transplant rejection in a transplant recipient comprising administering a dose of vitamin D compound effective to moderate transplant rejection, wherein the recipient has not suffered bone demineralization.

19. The method of claim 18 wherein the recipient's total bone mass has been increased after treatment with the vitamin D compound.

20. The method of claim 18 wherein the vitamin D compounds are 1α-hydroxy compounds.

21. The method of claim 20 wherein the compound is $1,25(OH)_2D_3$.

22. The method of claim 21 wherein the amount of vitamin D analog administered is between 0.5 and 50 μg per day per 160 pound patient.

23. The method of claim 21 wherein the amount of vitamin D analog administered is between 0.5 and 0.75 μg per day per 160 pound patient.

24. The method of claim 21 wherein the amount of vitamin D analog administered is between 0.5 and 1.5 μg per day per 160 pound person.

25. A method of moderating transplant rejection of a transplant recipient comprising the steps of orally administering to a transplant recipient an amount of the following compound effective to reduce transplant rejection:

wherein $X^1$ and $X^2$ are each selected from the group consisting of hydrogen and acyl;

wherein $Y^1$ and $Y^2$ can be H, or one can be O=aryl or O=alkyl and can have a β or α configuration; $Z^1=Z^2=H$ or $Z^1$ and $Z^2$ together are $CH_2$; and wherein R is an alkyl, hydroxyalkyl or fluoroalkyl group, or R may represent the following side chain:

wherein (a) may have an S or R configuration, $R^1$ represents hydrogen, hydroxy or O-acyl, $R^2$ and $R^3$ are each selected from the group consisting of alkyl, hydroxyalkyl and fluoroalkyl, or, when taken together represent the group —$(CH_2)_m$— wherein m is an integer having a value of from 2 to 5, $R^4$ is selected from the group consisting of hydrogen, hydroxy, fluorine, O-acyl, alkyl, hydroxyalkyl and fluoroalkyl, wherein if $R^5$ if hydroxyl or fluoro, $R^4$ must be hydrogen or alkyl, $R^5$ is selected from the group consisting of hydrogen, hydroxy, fluorine, alkyl, hydroxyalkyl and fluoroalkyl, or $R^4$ and $R^5$ taken together represent double-bonded oxygen, $R^6$ and $R^7$ taken together form a carbon-carbon double bond, $R^8$ may be H or $CH_3$, and wherein n is an integer having a value of from 1 to 5, and wherein the carbon at any one of positions 20, 22, or 23 in the side chain may be replaced by and O, S, or N atom, wherein the recipient's total bone mass has not decreased after the transplant.

26. The method of claim 25 wherein the recipient's bone mass increases.

27. The method of claim 25 wherein the compound is selected from the group of 1,25-dihydroxyvitamin $D_3$, 19-nor-1,25-dihydroxyvitamin $D_2$, 19-nor-21-epi-1,25-dihydroxyvitamin $D_3$, 1,25-dihydroxy-24-homo-22-dehydro-22E vitamin $D_3$, and 19-nor-1,25-dihydroxy-24-homo-22-dehydro-22E-vitamin $D_3$.

28. The method of claim 25 wherein the amount of compound administered is between 0.5 and 10 μg per day per 160 pound patient.

29. The method of claim 25 wherein the amount of compound administered is between 0.5 and 0.75 μq per day per 160 pound patient.

30. The method of claim 25 wherein the amount of compound administered is between 0.5 and 1.5 μg per day per 160 pound patient.

31. The method of claim 25 wherein the dose is given orally.

32. The method of claim 25 wherein the patient is on a low calcium diet.

33. The method of claim 25 wherein the administering is at night.

34. The method of claim 25 wherein the dose is given orally and wherein the patient is on a low-calcium diet and wherein the dose is 0.5–3.0 μg 1,25-dihydroxyvitamin $D_3$/day or its analog equivalent.

* * * * *

UNITED STATES PATENT AND TRADEMARK OFFICE
CERTIFICATE OF CORRECTION

PATENT NO. : 6,071,897  
DATED : June 6, 2000  
INVENTOR(S) : Hector F. DeLuca, et al.

Page 1 of 1

It is certified that error appears in the above-identified patent and that said Letters Patent is hereby corrected as shown below:

Column 2,  
Line 65: please delete "30" after -- 1996 --.

Column 4,  
Line 16: "1,125 (OH)$_2$D$_3$" should be -- 1,25 (OH)$_2$D$_3$ --.

Claims,  
Column 12,  
Line 45: "if" should be -- is --.  
Line 54: "and" should be -- an --.  
Line 56: "comprised" should be -- compromised --.

Column 14,  
Line 19: "if" should be -- is --.  
Line 28: "and" should be -- an --.

Signed and Sealed this

Twenty-fifth Day of September, 2001

Attest:

NICHOLAS P. GODICI  
*Attesting Officer*   *Acting Director of the United States Patent and Trademark Office*